US012004869B2

(12) United States Patent
Kiani et al.

(10) Patent No.: US 12,004,869 B2
(45) Date of Patent: Jun. 11, 2024

(54) SYSTEM TO MONITOR AND MANAGE PATIENT HYDRATION VIA PLETHYSMOGRAPH VARIABLITY INDEX IN RESPONSE TO THE PASSIVE LEG RAISING

(71) Applicant: Masimo Corporation, Irvine, CA (US)

(72) Inventors: Massi Joe E. Kiani, Laguna Niguel, CA (US); Bilal Muhsin, San Clemente, CA (US); Keith Ward Indorf, Riverside, CA (US)

(73) Assignee: Masimo Corporation, Irvine, CA (US)

( * ) Notice: Subject to any disclaimer, the term of this patent is extended or adjusted under 35 U.S.C. 154(b) by 1081 days.

(21) Appl. No.: 16/673,335

(22) Filed: Nov. 4, 2019

(65) Prior Publication Data

US 2020/0138368 A1 May 7, 2020

Related U.S. Application Data

(60) Provisional application No. 62/755,802, filed on Nov. 5, 2018.

(51) Int. Cl.
| | |
|---|---|
| *A61B 5/00* | (2006.01) |
| *A61B 5/024* | (2006.01) |
| *A61B 5/026* | (2006.01) |
| *A61B 5/029* | (2006.01) |
| *G16H 20/17* | (2018.01) |

(52) U.S. Cl.
CPC ........ *A61B 5/4848* (2013.01); *A61B 5/02405* (2013.01); *A61B 5/02433* (2013.01); *A61B 5/0261* (2013.01); *A61B 5/029* (2013.01); *A61B 5/4839* (2013.01); *A61B 5/4875* (2013.01);

(Continued)

(58) Field of Classification Search
None
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |

(Continued)

FOREIGN PATENT DOCUMENTS

WO     WO2016036946 A1 * 9/2015 ............. A61B 5/031

OTHER PUBLICATIONS

US 2022/0192529 A1, 06/2022, Al-Ali et al. (withdrawn)

(Continued)

*Primary Examiner* — Serkan Akar
(74) *Attorney, Agent, or Firm* — Knobbe, Martens, Olson & Bear, LLP

(57) ABSTRACT

Techniques for predicting fluid responsiveness or fluid unresponsiveness are described. A processor can determine a first prediction of fluid responsiveness or unresponsiveness based on a plethysmograph variability parameter associated with a plethysmograph waveform, and can determine a second prediction of fluid responsiveness or unresponsiveness based on a fluid responsiveness parameter that is associated with an elevation of one or more limbs of the patient. The processor can determine an overall prediction of fluid responsiveness or unresponsiveness based on the first and/or second predictions. Based on overall prediction, the processor can cause administration of fluids and/or termination of administration of fluids.

5 Claims, 8 Drawing Sheets

(52) U.S. Cl.
CPC ............ *A61B 5/7275* (2013.01); *A61B 5/742* (2013.01); *G16H 20/17* (2018.01)

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |

(56) References Cited

U.S. PATENT DOCUMENTS

| | | |
|---|---|---|
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |

(56) References Cited

U.S. PATENT DOCUMENTS

| | | |
|---|---|---|
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | Macneish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |

(56) References Cited

U.S. PATENT DOCUMENTS

| | | |
|---|---|---|
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,060,745 B2 | 6/2015 | Su et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |

(56) References Cited

U.S. PATENT DOCUMENTS

| | | |
|---|---|---|
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Al-Ali et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B2 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,433,776 B2 | 10/2019 | Al-Ali |
| 10,441,181 B1 | 10/2019 | Telfort et al. |
| 10,441,196 B2 | 10/2019 | Eckerbom et al. |
| 10,448,844 B2 | 10/2019 | Al-Ali et al. |

(56) References Cited

U.S. PATENT DOCUMENTS

| | | |
|---|---|---|
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0188760 A1 | 8/2008 | Al-Ali et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0099493 A1 | 4/2009 | O'Brien et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |

(56) References Cited

U.S. PATENT DOCUMENTS

| | | |
|---|---|---|
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1* | 11/2013 | Al-Ali .................. G16H 50/20 600/479 |
| 2013/0317322 A1 | 11/2013 | Andrijauskas |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |

(56) References Cited

U.S. PATENT DOCUMENTS

| | | |
|---|---|---|
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0216370 A1 | 8/2018 | Ishiguro et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274606 A1 | 9/2019 | Kiani et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |
| 2019/0307377 A1 | 10/2019 | Perea et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |

(56) References Cited

U.S. PATENT DOCUMENTS

| | | |
|---|---|---|
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |

OTHER PUBLICATIONS

Audimoolam et al (Predicting Fluid Responsiveness in Acute Liver Failure: A Prospective Study; Feb. 2017 • vol. 124 • No. 2 www.anesthesia-analgesia.org). (Year: 2017).*

Keller et al (Ability of pleth variability index to detect hemodynamic changes induced by passive leg raising in spontaneously breathing volunteers; Critical Care vol. 12 No 2, 2008). (Year: 2008).*

Loupec et al, Pleth variability index predicts fluid responsiveness in critically ill patients, Crit Care Med 2011 vol. 39, No. 2.*

Marik et al (Hemodynamic parameters to guide fluid therapy, Annals of Intensive Care 2011, 1:1). (Year: 2011).*

Dong et al., "Passive leg raising as an indicator of fluid responsiveness in patients with severe sepsis", World J Emerg Med vol. 3. No. 3, 2012.

"Pleth Variability Index: A Dynamic Measurement to Help Assess Physiology and Fluid Responsiveness," 2013 in 12 pages.

* cited by examiner

US 12,004,869 B2

SYSTEM TO MONITOR AND MANAGE PATIENT HYDRATION VIA PLETHYSMOGRAPH VARIABLITY INDEX IN RESPONSE TO THE PASSIVE LEG RAISING

RELATED APPLICATIONS

The application claims priority to U.S. Provisional Application No. 62/755,802, filed Nov. 5, 2018, entitled "System To Manage Patient Hydration," which is hereby incorporated by reference in its entirety.

TECHNICAL FIELD

The present disclosure relates generally to management of patient hydration and assessment of fluids responsiveness.

BACKGROUND

In the management of patients, the decision to administer fluids constitutes a common dilemma for physicians. For example, although a particular patient may be at least partially dehydrated (for example, due to preoperative fasting, sweat loss, urinary excretion, surgical blood loss, fluid shifts or other pathologic processes), the patient may not respond favorably to fluid administration (e.g., intravenous (IV) therapy). That is, the patient may not respond to fluid administration with an increase in stroke volume.

Accordingly, prior to or during fluid administration, it can be desirable to predict whether the patient's stroke volume (or, in some cases, cardiac output) will increase upon the fluid administration. Unfortunately, accurate prediction of an increase in stroke volume or cardiac output upon fluid loading, so-called fluid responsiveness, has proven to be difficult and/or unreliable.

SUMMARY

Techniques for predicting fluid responsiveness or fluid unresponsiveness are described. A processor can determine a first prediction of fluid responsiveness or unresponsiveness based on a plethysmograph variability parameter associated with a plethysmograph waveform, and can determine a second prediction of fluid responsiveness or unresponsiveness based on a fluid responsiveness parameter that is associated with an elevation of one or more limbs of the patient. The processor can determine an overall prediction of fluid responsiveness or unresponsiveness based on the first and/or second predictions. Based on overall prediction, the processor can cause administration of fluids and/or termination of administration of fluids.

In various embodiments, the system can identify a patient's hydration status based on physiological data associated with a patient. For example, in some cases, physiological data can correspond to a plethysmography (pleth) signal detected by a pulse oximetry device. Based on the physiological data, the system can identify a pleth variability parameter that is indicative of the hydration status of the patient, and can determine the hydration status of the patient based on the pleth variability parameter. As a non-limiting example, the pleth variability parameter can include a pleth variability index (PVI). For example, PVI can be obtained noninvasively, automatically, and continuously, and can quantify respiratory induced variations in a perfusion index. PVI can be an indicator of a patient's hydration status (for example, hydrated or dehydrated) and can be presented as a numerical value. In some cases, based on PVI the system can determine a hydration status of the patient.

In some cases, a method of determining fluid responsiveness of a patient includes receiving a sensor signal corresponding to a non-invasive physiological sensor. The non-invasive physiological sensor can be configured to emit light towards a tissue site of a patient, detect the light after it has interacted with the tissue site, and generate the sensor signal based at least in part on the detected light. The method can further include demodulating the sensor signal to generate a plethysmograph waveform including a plurality of pulses corresponding to pulsatile blood flow within the tissue site. The method can further include determining a plethysmograph variability parameter associated with the plethysmograph waveform. The plethysmograph variability parameter can quantify variations in the plethysmograph waveform. The method can further include determining a first prediction of fluid responsiveness based at least in part on the plethysmograph variability parameter. The method can further include determining a second prediction of fluid responsiveness based at least in part on a fluid responsiveness parameter that is associated with an elevation of one or more limbs of the patient. The method can further include outputting an indication of fluid responsiveness of the patient based at least in part on the first prediction of fluid responsiveness and the second prediction of fluid responsiveness.

The method of any of the preceding paragraphs and/or any of the methods disclosed herein may include any combination of the following steps or features described in this paragraph, among other features described herein. The plethysmograph variability parameter can correspond to a value associated with a pleth variability index (PVI). The fluid responsiveness parameter can include a measure of at least one of cardiac output, heart rate, or stroke volume. The method can further include determining a plurality of perfusion parameters based at least in part on the plethysmograph waveform. A particular perfusion parameter of the plurality of perfusion parameters can be determined based at least in part on a peak amplitude and a valley amplitude of a corresponding pulse of the plurality of pulses. Said determining the plethysmograph variability parameter can be based at least in part on a difference between a first and second perfusion parameter of the plurality of perfusion parameters relative to the first perfusion parameter of the plurality of perfusion parameters. The indication of fluid responsiveness of the patient can be an overall prediction of fluid responsiveness of the patient.

The method of any of the preceding paragraphs and/or any of the methods disclosed herein may include any combination of the following steps or features described in this paragraph, among other steps or features described herein. The method can be performed prior to administration fluids to the patient. The method can be performed during administration fluids to the patient. The elevation of the one or more limbs of the patient can be associated with a passive leg raising (PLR) test. The PLR test can be performed prior to administration of fluids to the patient. The PLR test can be performed during administration of fluids to the patient. The method can include performing an action based at least in part on the indication of the fluid responsiveness. The action can include at one of initiating administration of fluids to the patient, terminating the administration of the fluids to the patient, causing a display to display an indication of a recommendation for fluid administration, or causing the display to display an indication of a recommendation for termination of fluid administration. The indication of fluid responsiveness can indicate a response of stroke volume of the patient to fluid administration. The method can include determining a first confidence parameter corresponding to the first prediction of fluid responsiveness; and determining a second confidence parameter corresponding to the second prediction of fluid responsiveness. The fluid responsiveness of the patient can be further based at least in part on the first confidence parameter and the second confidence parameter.

In some cases, a system for determining fluid responsiveness of a patient can include a sensor interface and a processor in communication with the sensor interface. The sensor interface can be configured to connect to a non-invasive physiological sensor and to receive a sensor signal from the non-invasive physiological sensor. The non-invasive physiological sensor can be configured to emit light towards a tissue site of a patient, detect the light after it has interacted with the tissue site, and generate the sensor signal based at least in part on the detected light. The processor can be configured to determine a plethysmograph variability parameter associated with a plethysmograph waveform corresponding to the sensor signal. The plethysmograph waveform can include a plurality of pulses corresponding to pulsatile blood flow within the tissue site. The plethysmograph variability parameter can quantify variations in the plethysmograph waveform. The processor can be further configured to determine a first prediction of fluid responsiveness based at least in part on the plethysmograph variability parameter. The processor can be further configured to determine a second prediction of fluid responsiveness based at least in part on a fluid responsiveness parameter that is associated with an elevation of one or more limbs of the patient. The processor can be further configured to output an indication of fluid responsiveness of the patient based at least in part on the first prediction of fluid responsiveness and the second prediction of fluid responsiveness.

The patient monitoring device of any of the preceding paragraphs and/or any of the patient monitoring devices disclosed herein may include any combination of the following features described in this paragraph, among other features described herein. The plethysmograph variability parameter can correspond to a value associated with a pleth variability index (PVI). The fluid responsiveness parameter can include a measure of at least one of cardiac output, heart rate, or stroke volume. The elevation of the one or more limbs of the patient can be associated with a passive leg raising (PLR) test. The PLR test can be performed prior to administration of fluids to the patient. The PLR test can be performed during administration of fluids to the patient. The processor can be further configured to cause an action based on the fluid responsiveness of the patient, wherein the action can include at least one of initiating administration of fluids to the patient, terminating the administration of the fluids to the patient, causing a display to display an indication of a recommendation for fluid administration, or causing the display to display an indication of a recommendation for termination of fluid administration. The processor can be further configured to determine a first confidence parameter corresponding to the first prediction of fluid responsiveness; and determine a second confidence parameter corresponding to the second prediction of fluid responsiveness. The fluid responsiveness of the patient can be further based at least in part on the first confidence parameter and the second confidence parameter.

Any of the features of any of the methods described herein can be used with any of the features of any of the other methods described herein. Any of the features of any of the systems, devices, or methods illustrated in the figures or described herein can be used with any of the features of any of the other systems, devices, or methods illustrated in the figures or described herein.

BRIEF DESCRIPTION OF THE DRAWINGS

The following drawings and the associated descriptions are provided to illustrate embodiments of the present disclosure and do not limit the scope of the claims.

While the foregoing "Brief Description of the Drawings" references generally various embodiments of the disclosure, an artisan will recognize from the disclosure herein that such embodiments are not mutually exclusive. Rather, the artisan would recognize a myriad of combinations of some or all of such embodiments.

DETAILED DESCRIPTION

Figure 1:
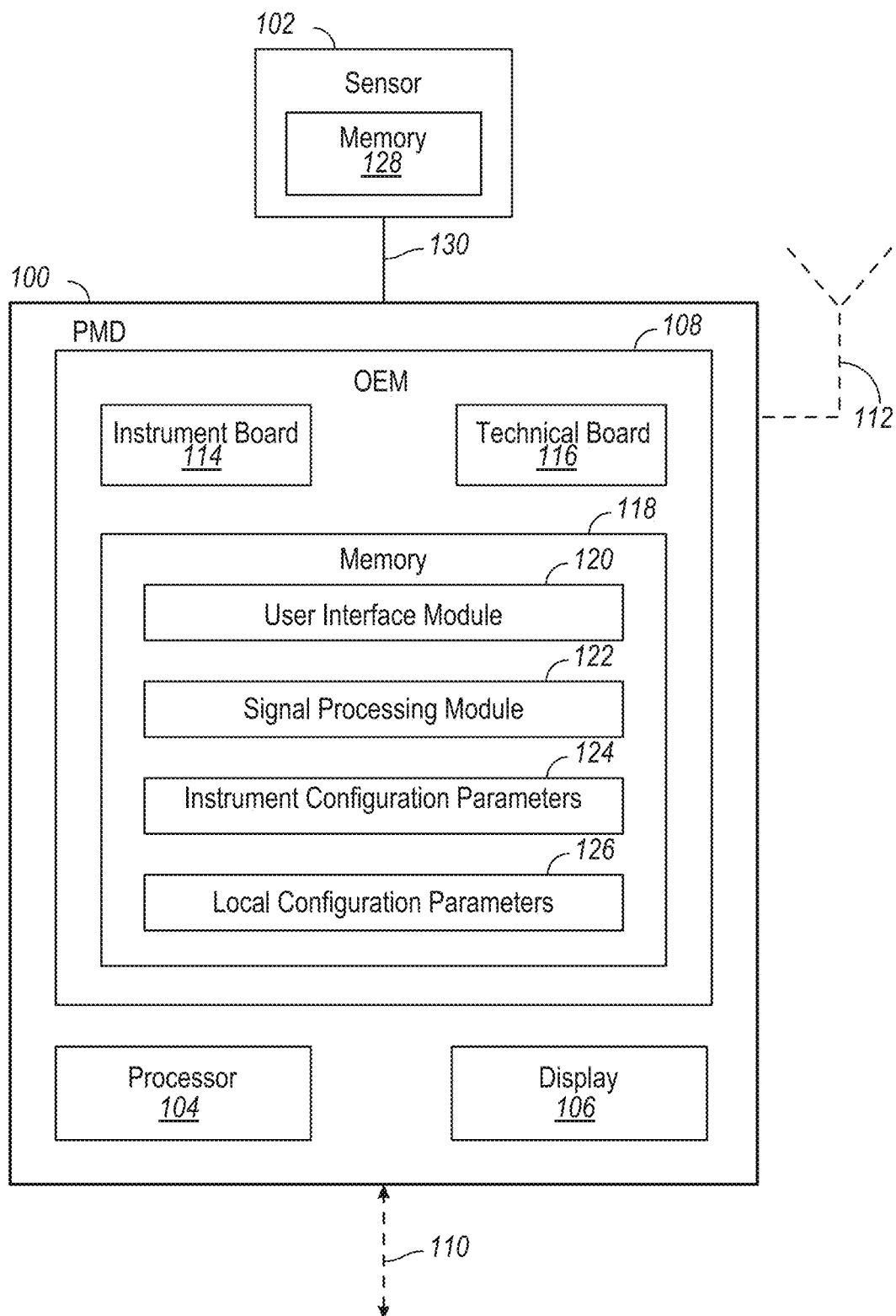
FIG. 1 is an example block diagram of a patient monitoring device.

FIG. 1 is an example block diagram of a patient monitoring device 100. The patient monitoring device can include a docked portable patient monitor 100, which may be referred to herein as the patient monitoring device 100. The patient monitoring device 100 may advantageously include an oximeter, co-oximeter, respiratory monitor, depth of sedation monitor, noninvasive blood pressure monitor, vital signs monitor or the like, such as those commercially available from Masimo Corporation of Irvine, CA, and/or disclosed in U.S. Patent Publication Nos. 2002/0140675, 2010/0274099, 2011/0213273, 2012/0226117, 2010/0030040; U.S. Patent Application Ser. Nos. 61/242,792, 61/387,457, 61/645,570, 13/554,908 and U.S. Pat. Nos. 6,157,850, 6,334,065, and the like.

The patient monitoring device 100 can include a first processor 104, a display 106, and an OEM board 108. The patient monitoring device 100 further includes one or more cables 110 and an antenna 112 for wired and wireless communication, respectively.

The OEM board 108 can include an instrument board 114, a core or technical board 116, and memory 118. In some cases, the memory 118 can include a user interface module 120, a signal processing module 122, instrument configuration parameters 124, and local configuration parameters 126.

The patient monitoring device 100 may communicate with a variety of noninvasive and/or minimally invasive sensors 102 such as optical sensors with light emission and detection circuitry, acoustic sensors, devices that measure blood parameters from a finger prick, cuffs, ventilators, ECG sensors, pulse oximeters, and the like.

One or more of the sensors 102 can be attached to a medical patient. The sensors 102 can obtain physiological information from a medical patient and transmit this information to the technical board 116 through cables 130 or through a wireless connection (not shown). The physiological information can include one or more physiological parameters or values and waveforms corresponding to the physiological parameters.

The technical board 116 can receive physiological information from the sensors 102. The technical board 116 can include a circuit having a second processor, which may be the same as the first processor 104, and input ports for receiving the physiological information. The technical board 116 can access the signal processing module 122 to process the physiological information in the second processor. In addition, the technical board 116 can include one or more output ports, such as serial ports. For example, an RS232, RS423, or autobaud RS232 (serial interface standard) port or a universal serial bus (USB) port may be included in the technical board 116.

The technical board 116 and the signal processing module 122 can include a sensor processing system for the patient monitoring device 100. In some cases, the sensor processing system generates waveforms from signals received from the sensors 102. The sensor processing system may also analyze single or multiparameter trends to provide early warning alerts to clinicians prior to an alarm event. In addition, the sensor processing system can generate alarms in response to physiological parameters exceeding certain safe thresholds.

Example alerts include no communication with the patient monitoring device 100, alarm silenced on the patient monitoring device 100, instrument low battery (patient monitoring device 100), transmitter low battery, and/or indications of fluid responsiveness. Example physiological parameters include $SpO_2$ levels, high and low $SpO_2$, high and low PR, HbCO level, HbMET level, pulse rate, perfusion index, signal quality, HbCO, HbMET, PI, and desat index. Additional example alarms include $SpO_2$ alarms, high and low $SpO_2$ alarms, high and low PR, HbCO alarms, HbMET alarms, pulse rate alarms, no sensor alarms, sensor off patient alarms, sensor error, low perfusion index alarm, low signal quality alarm, HbCO alarm, HbMET alarm, PI trend alarm, and desat index alarm.

The instrument board 114 can receive the waveforms, alerts, alarms, and the like from the technical board 116. The instrument board 114 can include a circuit having a third processor, which may be the same as the first processor 104, and input ports for receiving the waveforms, alerts, and alarms from the technical board 116 and output ports for interfacing with the display 106, a speaker or other device capable of producing an audible indication. The instrument board 114 can access the user interface module 120 to process the waveforms, alerts, and alarms to provide indications of the waveforms, alerts, alarms or other data associated with the physiological parameters monitored by the sensors 102. The indications can be displayed on the display 106. In addition or alternatively, the alerts and alarms are audible. The indications, alerts, and alarms can be communicated to end-user devices, for example, through a hospital backbone, a hospital WLAN 16, and/or the Internet.

Additionally, the instrument board 114 and/or the technical board 116 may advantageously include one or more processors and controllers, busses, all manner of communication connectivity and electronics, memory, memory readers including EPROM readers, and other electronics recognizable to an artisan from the disclosure herein. Each board can include substrates for positioning and support, interconnect for communications, electronic components including controllers, logic devices, hardware/software combinations and the like to accomplish the tasks designated above and others.

An artisan will recognize from the disclosure herein that the instrument board 114 and/or the technical board 116 may include a large number of electronic components organized in a large number of ways.

Because of the versatility needed to process many different physiological parameters, the technical board 116 can further include a revision number or other indication of the circuit design and capabilities of a specific technical board 116.

Likewise, because of the versatility needed to display the processed physiological parameters for use by many different end users, the instrument board 114 can further include a revision number or other indication of the circuit design and capabilities of the specific instrument board.

Software is also subject to upgrading to increase its capabilities. The signal processing module 122 can further include a version number or other indication of the code found in the specific signal processing module 122. Likewise, the user interface module 120 can further include a version number or other indication of the code found on the specific user interface module 120.

Some or all of the serial numbers, the model numbers, and the revision numbers of the technical board 116 and the instrument board 114 that include the specific patient monitoring device 100 can be stored in the instrument configuration parameters 124. Further, the version numbers of the signal processing module 122 and the user interface module 120 are stored in the instrument configuration parameters 124. The instrument configuration parameters 124 can further include indications of the physiological parameters that are enabled, and indications of the physiological parameters that are capable of being enabled for the patient monitoring device 100.

The location of the patient monitoring device 100 can affect the sensitivity at which a physiological parameter is monitored. For example, a physiological parameter may be monitored with greater sensitivity when the patent monitoring device 100 is located in the neonatal intensive care unit (NICU), OR or surgical ICU than when it is located in an adult patient's room. In some cases, the location of the patient monitoring device 100 may affect the availability of the device for another patient. For example, a patient monitoring device 100 located in the hospital discharge area may be available for another patient, whereas one located in a patient's room may not be available anytime soon.

The local configuration parameters 126 can include a location of the patient monitoring device 100 within the facility, an indication of whether the device is configured for adult or pediatric monitoring, and the like.

The sensor 102 can include memory 128. The memory 128 can include information associated with the sensor 102, such as, but not limited to a sensor type, a sensor model number, a sensor revision number, a sensor serial number, and the like.

The patient monitoring device 100 can include a Radical-7® Rainbow SET Pulse Oximeter by Masimo Corporation, Irvine, CA The OEM board 108 can be produced by Masimo Corporation, Irvine, CA and used by others to produce patient monitoring devices.

Figure 2A:
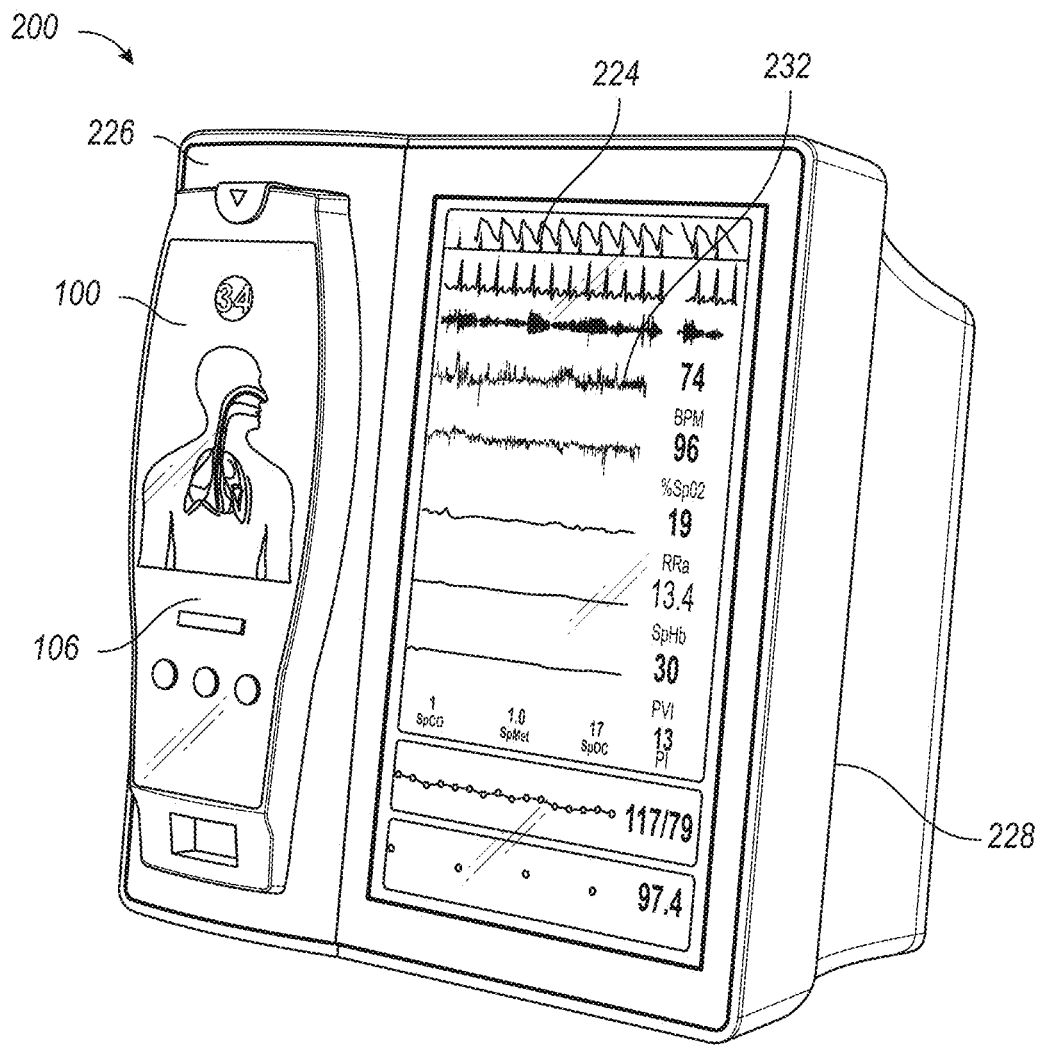
FIG. 2A is a perspective view of an example patient monitoring device including a hub and the patient monitoring device of FIG. 1.

FIG. 2A illustrates a perspective view of an example patient monitoring device, such as a medical monitoring hub with the docked portable patient monitoring device 100, the combination of which may also be referred to herein as a patient monitoring device or patient monitoring system 200. The hub includes a display 224, and a docking station 226, which can be configured to mechanically and electrically mate with the portable patient monitoring device 100, each housed in a movable, mountable and portable housing 228. The housing 228 includes a generally upright inclined shape configured to rest on a horizontal flat surface, although the housing 228 can be affixed in a wide variety of positions and mountings and include a wide variety of shapes and sizes.

The display 224 may present a wide variety of measurement and/or treatment data in numerical, graphical, waveform, or other display indicia 232. The display 224 can occupy much of a front face of the housing 228; although an artisan will appreciate the display 224 may include a tablet or tabletop horizontal configuration, a laptop-like configuration or the like. Other examples may include communicating display information and data to a table computer, smartphone, television, or any display system recognizable to an artisan. The upright inclined configuration of FIG. 2A presents display information to a caregiver in an easily viewable manner. The patient monitoring device 200 may display information for a variety of physiological parameters, such as but not limited to oxygen saturation (SpO2), hemoglobin (Hb), oxyhemoglobin (HbO2), total hemoglobin, carboxyhemoglobin, methemoglobin, perfusion index (Pi), pulse rate (PR) of blood pressure, temperature, electrocardiogram (ECG), motion data, accelerometer data, respiration, continuous blood pressure, pleth variability index (PVI), oxygen content, oxygen reserve index, acoustic respiration rate (RRa), respiration rate from the pleth, cardiac output, stroke volume, and/or fluid responsiveness.

Figure 2B:
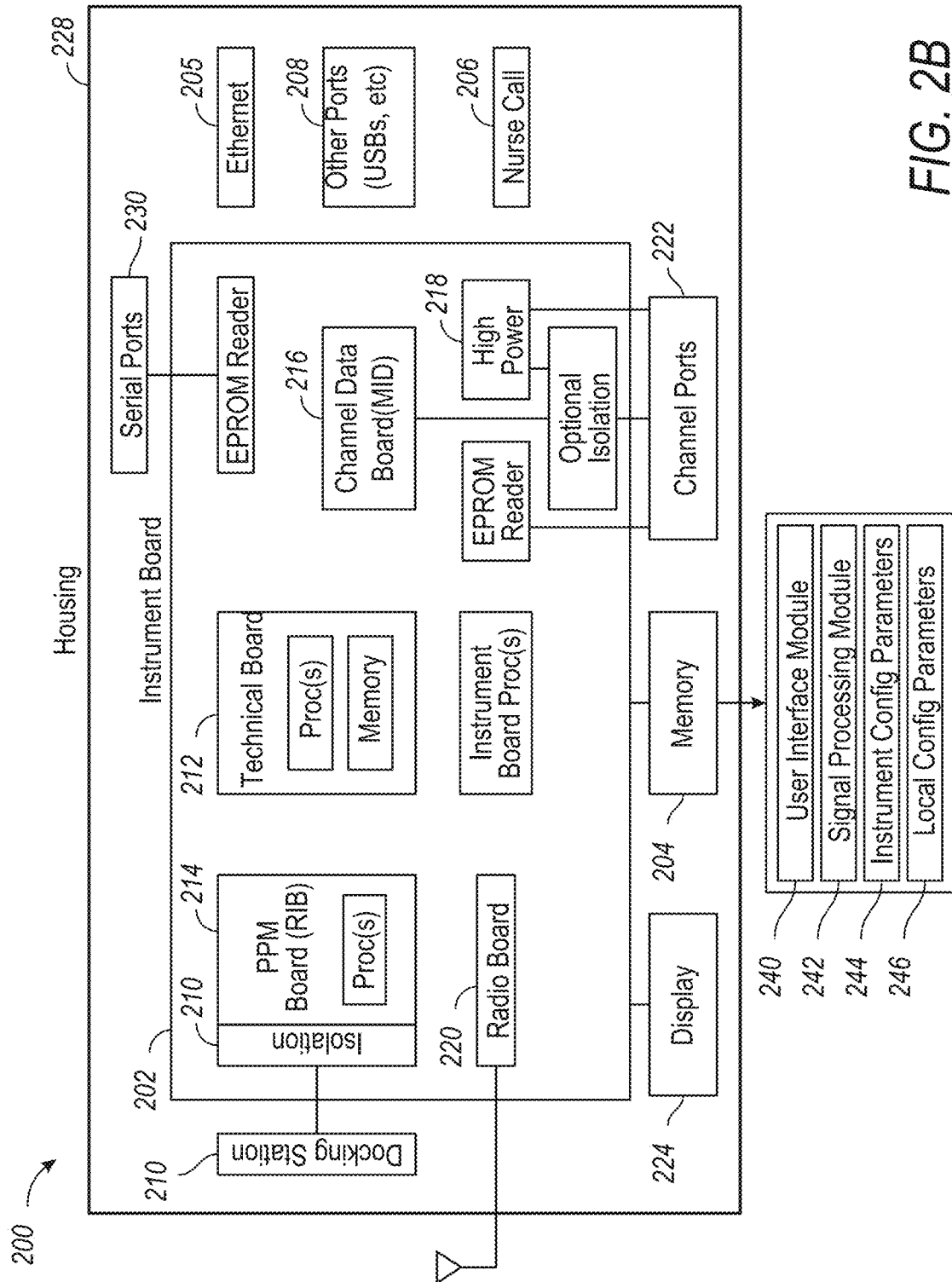
FIG. 2B illustrates an example hardware block diagram of the hub of FIG. 2B.

FIG. 2B illustrates a simplified example hardware block diagram of the patient monitoring device 200. As shown in FIG. 2B, the housing 228 of the patient monitoring device 200 positions and/or encompasses an instrument board 202, a core or technical board 212, the display 224, memory 204, and the various communication connections, including serial ports 230, channel ports 222, Ethernet ports 205, nurse call port 206, other communication ports 208 including standard USB, or the like, and a docking station interface 210. The instrument board 202 can include one or more substrates including communication interconnects, wiring, ports and the like to enable the communications and functions described herein, including inter-board communications. The technical board 212 includes the main parameter, signal, and other processor(s) and memory. A portable monitor board ("RIB") 214 includes patient electrical isolation for the monitor 100 and one or more processors. A channel board ("MID") 216 controls the communication with the channel ports 222 including optional patient electrical isolation and power supply 218, and a radio board 220 includes components configured for wireless communications.

Additionally, the instrument board 202 and/or the technical board 212 may advantageously include one or more processors and controllers, busses, all manner of communication connectivity and electronics, memory, memory readers including EPROM readers, and other electronics recognizable to an artisan from the disclosure herein. Each board can include substrates for positioning and support, interconnect for communications, electronic components including controllers, logic devices, hardware/software combinations and the like to accomplish the tasks designated above and others.

An artisan will recognize from the disclosure herein that the instrument board 202 and or the technical board 212 may include a large number of electronic components organized in a large number of ways.

Because of the versatility needed to process many different physiological parameters, the technical board 212 can further include a revision number or other indication of the circuit design and capabilities of a specific technical board 212.

Likewise, because of the versatility needed to display the processed physiological parameters for use by many different end users, the instrument board 202 can further include a revision number or other indication of the circuit design and capabilities of the specific instrument board 202.

The memory 204 can include a user interface module 240, a signal processing module 242, instrument configuration parameters 244, and local configuration parameters 246.

The instrument board 202 can access the user interface module 240 to process the waveforms, alerts, and alarms to provide indications of the waveforms, alerts, alarms or other data associated with the physiological parameters for the patient monitoring device 200. The technical board 212 can access the signal processing module 242 to process the physiological information for the patient monitoring device 200.

Software for the patient monitoring device 200 is also subject to upgrading to increase its capabilities. The signal processing module 242 can further include a version number or other indication of the code found in the specific signal processing module 242. Likewise, the user interface module 240 can further include a version number or other indication of the code found on the specific user interface module 240.

Some or all of the serial numbers, the model numbers, and the revision numbers of the technical board 212 and the instrument board 202 that include the specific patient medical monitoring hub 150 can be stored in the instrument configuration parameters 244. Further, the version numbers of the signal processing module 242 and the user interface module 240 can be stored in the instrument configuration parameters 244. The instrument configuration parameters 244 further include indications of the physiological parameters that are enabled, and indications of the physiological parameters that are capable of being enabled for the patient monitoring device 200.

The local configuration parameters 246 can include a location of the patient monitoring device 200 within the facility, an indication of whether the device is configured for adult or pediatric monitoring, and the like.

The patient monitoring device 200 can include a Root® Patient Monitoring and Connectivity Platform by Masimo Corporation, Irvine, CA that includes the Radical-7® also by Masimo Corporation, Irvine, CA.

Figure 3:
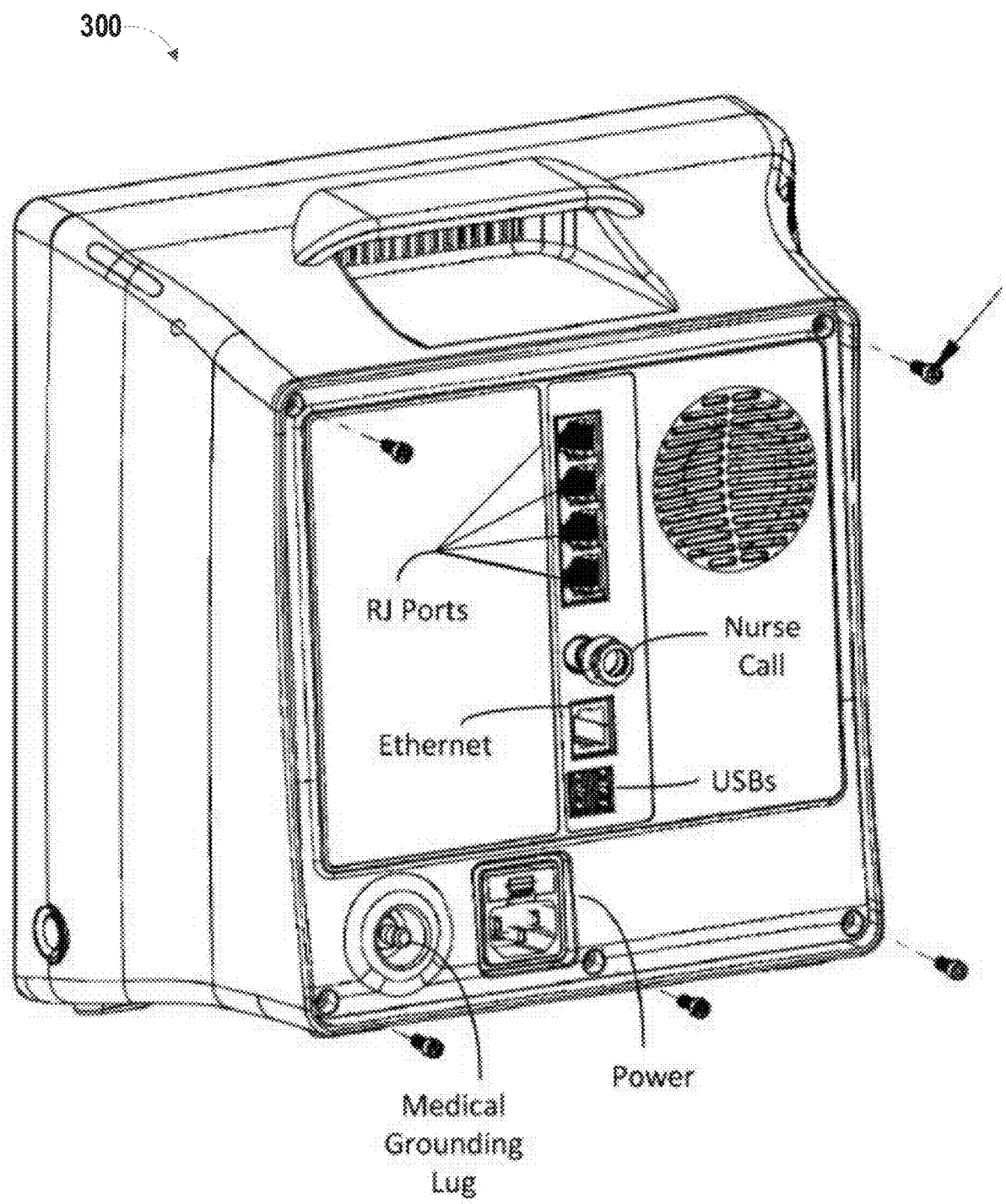
FIG. 3 illustrates a perspective view of the back of the patient monitoring device of FIG. 2A.

FIG. 3 illustrates an example perspective view of the back of the patient monitoring device 200 of FIG. 2A, showing an example serial data inputs. The inputs can include RJ 45 ports. As is understood in the art, these ports include data ports similar to those found on computers, network routers, switches and hubs. A plurality of these ports can be used to associate data from various devices with the specific patient identified in the patient monitoring device 200. FIG. 3 also shows a speaker, the nurse call connector, the Ethernet connector, the USBs, a power connector and a medical grounding lug.

Patient Hydration

Dehydration is a condition that can occur when the loss of body fluids, mostly water, exceeds the amount that is taken in. For example, the body is constantly losing fluids through breathing, sweat loss, and urinary excretion. In addition, the body can lose fluids as a result of preoperative fasting, surgical blood loss, fluid shifts or other pathologic processes. With dehydration, more water is moving out of individual cells and then out of the body than the amount of water that is taken in. Medically, dehydration usually means a person has lost enough fluid so that the body begins to lose its ability to function normally.

The severity of dehydration can vary based on the amount of fluids in the patient's body. For example, in some cases, dehydration can be classified based on levels or a degree of dehydration. For instance, in some cases, if a patient is dehydrated, a level of the patient's dehydration can be classified as one of mild dehydration, moderate dehydration, or severe dehydration, or somewhere in between. In some cases, mild dehydration corresponds to a 3% to 5% drop in fluids as compared to normal or average fluid levels of the patient, moderate dehydration corresponds to a 6% to 10% drop in fluids as compared to normal or average fluid levels of the patient, and severe dehydration corresponds to more than a 10% drop in fluids as compared to normal or average fluid levels of the patient. However, it will be understood that the range or categorizations of degrees of dehydration can vary across embodiments. For example, in some cases, patient hydration can be binary: dehydrated or not dehydrated. Furthermore, in some cases, patient hydration can correspond to a sliding scale, such as a scale from 0 to 100. Further still, the ranges or categorizations of degrees of dehydration can vary based on a patient's age, gender, weight, etc.

Dehydration can itself be dangerous. Furthermore, dehydration can cause common conditions including, but not limited to, constipation, falls, urinary tract infections, pressure ulcers, malnutrition, incontinence, confusion, acute kidney injury, cardiac disease or venous thromboembolism. For some patients, preventing or treating dehydration is difficult without assistance. For instance, a patient may not be able to drink or consume fluids. In some such cases, fluids can be administered to the patient, for example, intravenously. However, in many instances, dehydrated can be difficult to detect or predict. Accordingly, it can be desirable to gage an accurate assessment of patient hydration or dehydration.

In some cases, the system can obtain an accurate assessment of patient hydration or dehydration (non-limiting example, whether a hydration threshold is satisfied or not satisfied) using physiological data of the patient. For example, the system can include (or receive signals from) a pulse oximeter, which can be positioned on the patient. In some cases, the pulse oximeter can detect a pleth signal, and can communicate the pleth signal, or an indication thereof, to the system.

Figure 4:
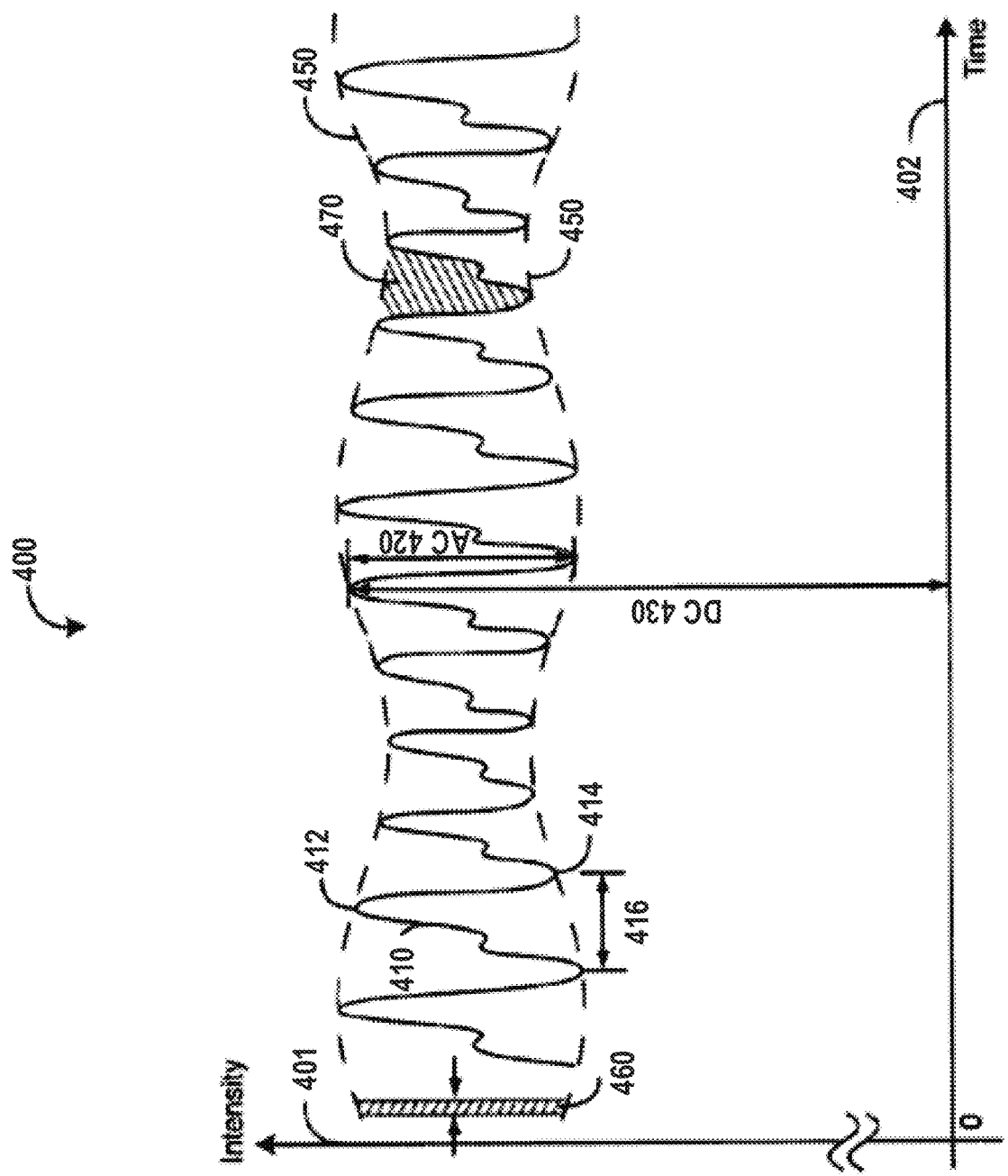
FIG. 4 illustrates a pleth signal plotted on an intensity axis versus a time axis.

FIG. 4 illustrates a pleth signal 400 plotted on an intensity axis 401 versus a time axis 402. The pleth signal 400 has multiple pulses 410, which correspond to pulsatile blood flowing within a tissue site. As illustrated, each pulse 410 is characterized by a plurality of features such as a peak amplitude 412, valley amplitude 414, and period 416. Further, pleth signal 400 defines a pleth envelope 450 interpolated from pulse peaks 412 and pulse valleys 414.

Perfusion values, or a perfusion index (PI), can be defined for each pulse 410. PI generally reflects the amplitude of the waveform and is calculated as the pulsatile infrared signal (AC 420 or variable component), indexed against the non-pulsatile infrared signal (DC 430 or constant component). PI can be expressed as a percentage (for example, 0.02-20%). In some cases, PI is the ratio of the pulsing blood to non-pulsing blood flow, and can be determined using the following equation:

$$PI = \frac{AC}{DC} \quad \text{(Equation 1)}$$

where AC can represent a peak amplitude 412 minus a valley amplitude 414 for a particular pulse, and DC can represent a peak amplitude 412 for a particular pulse. Among other things, PI can be used to indicate a strength of blood flow a measurement site. In some cases, DC can represent a value other than peak amplitude 412, such as a valley amplitude 414 or an average of peak amplitude 412 and valley amplitude 414, to name a few.

In some cases, a patient monitoring device, such as the patient monitoring device 100 of FIG. 1, can identify a pleth variability parameter that is responsive to variations of the pleth. In some cases, a pleth variability parameter is a clinically useful hemodynamic measurement because it can respond to changes in patient physiology, thereby acting as a useful indicator of various physiological conditions or the efficacy of treatment for those conditions. Advantageously, pleth variability measures may provide a numerical indication of a person's physical condition or health. For example, changes in a pleth variability parameter may be representative of changes in physiologic factors such as patient hydration.

One variability measure is a Pleth Variability Index (PVI or PVi®) (developed by Masimo® Corporation, Irvine, CA, USA)) as described in greater detail in U.S. Pub. No. 2008/0188760, filed Dec. 7, 2007, and entitled "PLETHYSMOGRAPH VARIABILITY PROCESSOR," which is hereby incorporated by reference herein in its entirety.

PVI can be based on perfusion index (PI) variations during a respiratory cycle. For example, PVI can be a measure of dynamic changes in PI that occur during one or more complete respiratory cycles. As illustrated from Equation 2 below, the calculation for PVI can be accomplished by measuring changes in PI over a time interval where one or more complete respiratory cycles have occurred, and can be determined using the following equation:

$$PVI = \frac{PI_{max} - PI_{min}}{PI_{max}} * 100 \quad \text{(Equation 2)}$$

In some cases, PVI can be automatically or continuously calculated and can represent respiratory variations in the plethysmographic waveform. Furthermore, in some cases, PVI may be indicative of or correlated with patient hydration or dehydration. As a non-limiting example, in some cases, a relatively lower PVI can indicate that the patient's hydration level does not satisfy a hydration threshold (e.g., the patient is dehydrated). As a corollary, a relatively high PVI can indicate that the patient's hydration level satisfies a hydration threshold (e.g., the patient is not dehydrated). However, it will be understood that, in some cases, a relatively low PVI can indicate that the patient's hydration level satisfies a hydration threshold and/or a relatively high PVI can indicate that the patient's hydration level does not satisfy a hydration threshold. In some cases, PVI can be displayed as a percentage (numerical value) and/or a trend graph. Similarly, the patient monitoring device can display (or cause a display to display) an indication of the patient's hydration status (for example, dehydrated, hydrated, no dehydrated, mildly dehydration, moderately dehydration, or severely dehydration mild dehydration, etc.) based at least in part on PVI. As another example, in some cases, the patient monitoring device can provide an indication to (or control a device to) initiate administration of fluids, continue administration of fluids, or terminate administration of fluids based at least in part on PVI. For example, in some cases, based on a determination that the patient is dehydrated, the patient monitoring device can provide an indication to (or control a device to) initiate administration of fluids or continue administration of fluids. As a corollary, in some cases, based on a determination that the patient is not dehydrated, the patient monitoring device can provide an indication to (or control a device to) terminate administration of fluids.

Cardiac Output

Cardiac output can refer to an amount or volume of blood that the heart pumps through the circulatory system, and is generally expressed in liters per minute. Sufficient cardiac output (that is, a cardiac output that satisfies a threshold cardiac output) helps keep blood pressure at the levels needed to supply oxygen-rich blood to the brain and other vital organs. In some cases, cardiac output can be calculated using the following equation:

$$CO = HR \times SV \qquad \text{(Equation 3)}$$

where CO is the Cardiac output, HR is heart rate (e.g., the number of heart beats per minute (bpm)), and SV is stroke volume (e.g., the amount of blood pumped from the left (or right) ventricle of the heart in one contraction). Accordingly, the cardiac output can be a function of heart rate and stroke volume, and thus, in some cases, the factors affecting stroke volume or heart rate may also affect cardiac output.

As a non-limiting example, for someone weighing about 70 kg (154 lbs.), a healthy heart with a normal cardiac output can pump about 5 to 6 liters of blood every minute when a person is resting. During exercise, the body may need three or four times its normal cardiac output, because the muscles need more oxygen. Thus, during exercise, the heart typically beats faster (known as increased heart rate) so that more blood flows out to the body. The heart can also increase its stroke volume by pumping more forcefully or increasing the amount of blood that fills the left ventricle before it pumps. Generally, an increase in cardiac output can be favorable or desired, as it can indicate an increase in the supply of oxygen-rich blood. In contrast, a decrease in cardiac output can be unfavorable or not desired, as it can indicate a decrease in the supply of oxygen-rich blood.

Fluid Responsiveness

Volume expansion can be applied to increase an amount of fluid present in a patient's body, and is frequently used before, during, or after surgery to correct dehydration or fluid deficits created by, for example, preoperative fasting, surgical blood loss, sweat loss, urinary excretion, fluid shifts or other pathologic processes. Techniques for volume expansion include, among other methods, oral rehydration therapy (for example, drinking), intravenous therapy (for example, delivering liquid substances directly into a vein), rectal therapy (for example, with a Murphy drip), or by hypodermoclysis (for example, the direct injection of fluid into the subcutaneous tissue).

In general, the objective of volume expansion is to improve oxygen delivery or overall hemodynamic function. However, some patients may not respond to volume expansion with improved oxygen delivery or improved overall hemodynamic function. For example, these patients may not respond to the volume expansion with an increase in stroke volume or cardiac output. In these patients, volume expansion can be either ineffective or deleterious, and can result in worsening oxygen delivery, inducing systemic and pulmonary edema or, in some cases, cardiac failure. In some cases, patients that do not respond to volume expansion with improved oxygen delivery or improved overall hemodynamic function are referred to as being fluid unresponsive. In some cases, patients that do respond to volume expansion with improved oxygen delivery or improved overall hemodynamic function are referred to as being fluid responsive. Thus, in some cases, a patient can be categorized as fluid unresponsive or fluid responsive based on how he or she will respond to volume expansion (sometimes referred to as a patient's fluid responsiveness).

As described herein, some patient's may be fluid unresponsive. Thus, it can be important to determine or predict a patient's fluid responsiveness (e.g. how a patient will respond to volume expansion) prior to administering fluids. In other words, prior to fluid administration, it can be important to determine or predict a patient's fluid responsiveness (or how fluid administration will affect a patient's cardiac output). A patient identified as someone that will respond to volume expansion with an increase in cardiac output such that the cardiac output satisfies a threshold cardiac output (or that the increase in cardiac output satisfies a threshold increase in cardiac output) can be classified as fluid responsive. In contrast, a patient identified as someone that will not respond to volume expansion with a cardiac output that satisfies a threshold cardiac output can be classified as fluid unresponsive. In some cases, an indication of a patient's fluid responsiveness can include an indication that the patient is fluid responsive, fluid unresponsive, or somewhere in between.

Although some static and dynamic cardiopulmonary indices have been used to predict fluid responsiveness, many of these measures generally have low predictive value, or can risk fluid overload (the condition of having too much fluid in the body, or the state of one of the chambers of the heart in which too large a volume of blood exists within it for it to function efficiently). For example, a fluid challenge can include administering fluids to patients in order to assess their response to fluid therapy and guide further treatment decisions. By administering a small amount of fluid in a short period of time, the clinician can assess the patient's fluid responsiveness. However, because volume expansion includes administering fluid to the patient, a fluid challenge can risk fluid overload.

Passive Leg Raising (PLR) Test

In some cases, the system can utilize information obtained as a result of the patient performing or being administered a passive leg raising (PLR) test to determine the patient's fluid responsiveness. The PLR test can vary across embodiments, but is generally a non-invasive, bedside test that involves elevating a patient's legs, and can be used to evaluate whether a patient will benefit from volume expansion. In some cases, the PLR test can be used to determine whether cardiac output respond such that it satisfies or does not satisfy a cardiac output threshold as a result of volume expansion.

In general, the PLR test involves raising the legs of a patient (without her active participation), which causes gravity to pull blood from the legs, thus increasing circulatory volume available to the heart, sometimes known as cardiac preload. The PLR test can be performed with the patient's active participation. For instance, the patient can actively raise his or legs. The PLR test can be performed with the patient's active participation. By transferring a volume of blood (for example, around 300 mL) from the lower body toward the heart, PLR mimics a fluid challenge. However, no fluid is infused and the hemodynamic effects are rapidly reversible, thereby avoiding the risks of fluid overload.

A method for performing a PLR test can include a sequence of steps. For example, the PLR test generally includes some combination of the following steps: (1) placing the patient in a semi-recumbent position (the patient's head and torso are positioned upright at an angle of about 45° relative to the patient's legs, which are resting flat on the table); (2) assessing the cardiac output. Here, the patient's heart rate, stroke volume, or the like can be identified by the system, or cardiac output can be determined; (3) moving the patient to a recumbent position (the patient's legs are raised and torso is lowered, where, ultimately, the patient is lying on her back with her feet raised at an angle of about 45°. Here, it may be beneficial not to have the patients elevate her legs manually because it may provoke pain, discomfort, or awakening that can cause adrenergic stimulation, giving false readings of cardiac output by increasing heart rate); (4) re-assessing the cardiac output. Here, the patient's heart rate, stroke volume, or the like can be identified by the system, or cardiac output can be determined; (5) returning the patient to a semi-recumbent position; and (6) re-assessing the cardiac output. Here, the patient's heart rate, stroke volume, or the like can be identified by the system, or cardiac output can be determined.

In general, the PLR test can be can used to assess fluid responsiveness without any fluid challenge, where the latter can lead to fluid overload. The real-time effects of the PLR test on hemodynamic parameters such as blood pressure, heart rate, or cardiac output can be used to guide the assessments on the patient's fluid responsiveness. For example, in some cases, if the patient's cardiac output responds such that it satisfies a threshold cardiac output, then it can be determined that the patient is fluid responsive. In contrast, in some cases, if the patient's cardiac output responds such that it does not satisfy a threshold cardiac output, then it can be determined that the patient is fluid unresponsive.

Flow Diagrams

Figure 5:
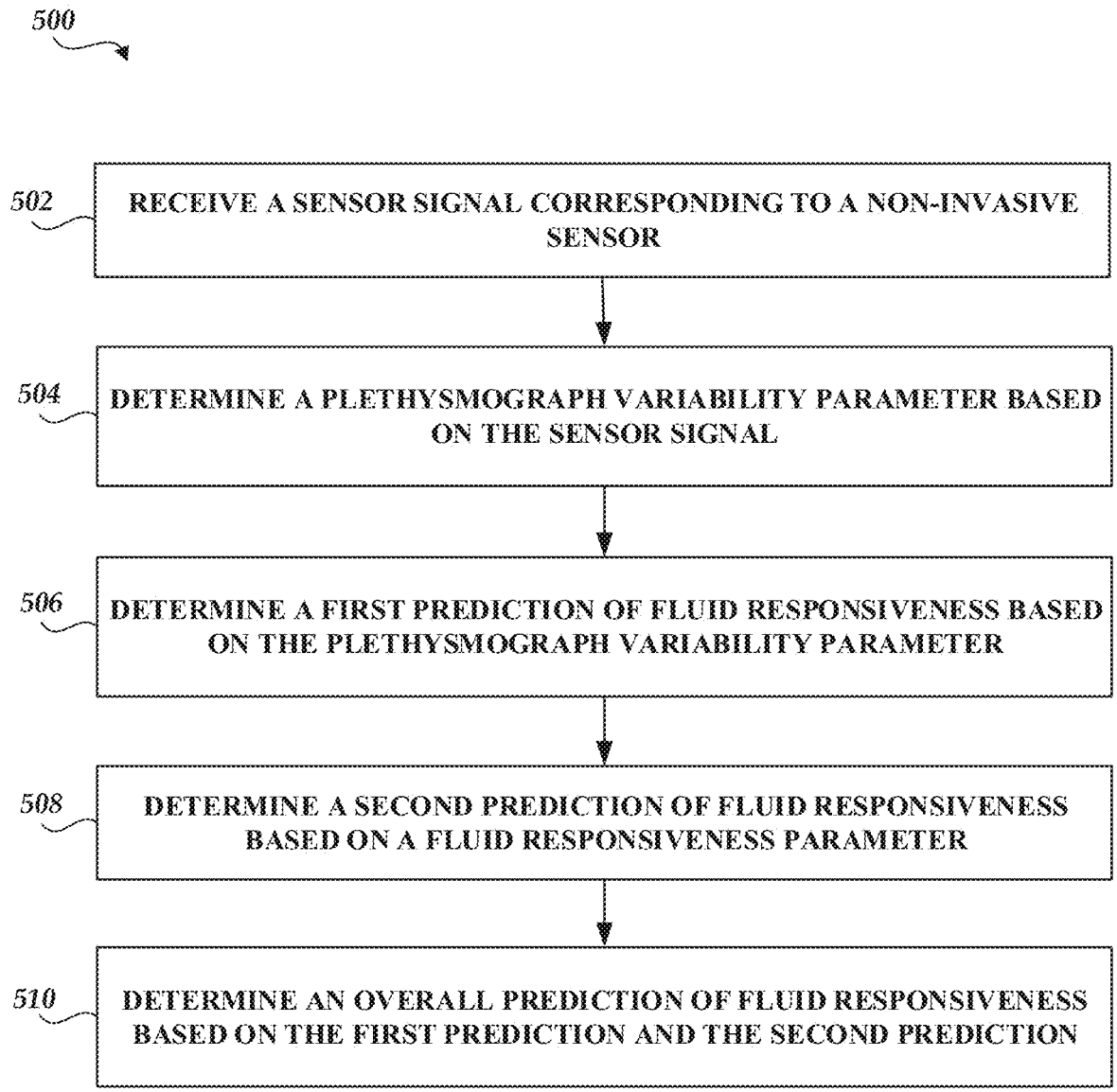
FIG. 5 is a flow diagram illustrative of an embodiment of a routine for assessing or predicting fluid responsiveness.

FIG. 5 is a flow diagram illustrative of an embodiment of a routine 500, implemented by a processor, for assessing or predicting fluid responsiveness. One skilled in the relevant art will appreciate that the elements outlined for routine 500 can be implemented by one or more computing devices that are associated with the system 200, such as the processor 104 or the monitoring device 100. Accordingly, routine 500 has been logically associated as being generally performed by the processor 104 of FIG. 1. However, the following illustrative embodiment should not be construed as limiting. Furthermore, it will be understood that the various blocks described herein with reference to FIG. 5 can be implemented in a variety of orders. For example, the processor 104 can implement some blocks concurrently or change the order, as desired. Furthermore, it will be understood that fewer, more, or different blocks can be used as part of the routine 500.

At block 502, the processor 104 receives a sensor signal corresponding to a non-invasive physiological sensor. As described herein, the non-invasive physiological sensor, such as sensor 102 of FIG. 1, can include at least one emitter configured to emit light at one or more wavelengths. Further, the non-invasive sensor can include a detector configured to detect the light from the least one emitter after the light has interacted with the tissue site of a patient, and generate the sensor signal based at least in part on the detected light. For example, the non-invasive physiological sensor can be attached to the patient, such as to the patient's finger.

At block 504, the processor 104 determines a plethysmograph variability parameter based at least in part on the sensor signal. In some cases, the plethysmograph variability parameter can includes a value that relates or quantifies changes in patient physiology. For example, in some cases, the plethysmograph variability parameter can reflect variations that occur during the respiratory cycle or changes in physiologic factors such as changes in fluid responsiveness, volemia, ventricular preload, etc.

The plethysmograph variability parameter can be determined using one or more of various techniques, such as any one or more of the techniques disclosed in U.S. Patent Publication No. 2013/0296713, filed Apr. 8, 2013, which is hereby incorporated by reference in its entirety. For example, the processor 104 can determine perfusion values, or a perfusion index (PI), from pulses of a plethysmograph waveform that corresponds to the sensor signal. Furthermore, the processor 104 can determine the plethysmograph variability parameter based on the perfusion values or the PI. For instance, the determination of the plethysmograph variability parameter can include calculating a difference between perfusion values and normalizing the difference. In some cases, the plethysmograph variability parameter corresponds to one or more plethysmograph variability index (PVI) values. For example, a PVI value can be a measure of the dynamic changes in the Perfusion Index (PI) that occur during one or more complete respiratory cycles.

At block 506, the processor 104 determines a prediction of fluid responsiveness or unresponsiveness based at least in part on the plethysmograph variability parameter. For example, in some cases, the plethysmograph variability parameter includes a numerical value. In some such cases, a relatively higher plethysmograph variability parameter may indicate fluid responsiveness. For example, a higher plethysmograph variability parameter may indicate more variance in the perfusion values and a greater likelihood that the patient will respond to fluid administration with an increase in cardiac output. As a corollary, in some such cases, a relatively lower plethysmograph variability parameter may indicate fluid unresponsiveness. For example, a lower plethysmograph variability parameter may indicate less variance in the perfusion values and therefore a lower likelihood that the patient will respond to fluid administration with an increase in cardiac output.

In some cases, the processor 104 can further determine a confidence value associated with the prediction of fluid responsiveness or unresponsiveness. For example, in some cases, the confidence in a prediction of fluid responsiveness increases (i.e., a higher confidence) as the plethysmograph variability parameter increases and decreases (i.e., a lower confidence) as the plethysmograph variability parameter decreases. As a corollary, in some cases, the confidence in a prediction of fluid unresponsiveness increases as the plethysmograph variability parameter decreases and decreases as the plethysmograph variability parameter increases.

At block 508, the processor 104 determines a prediction of fluid responsiveness or unresponsiveness based at least in part on a fluid responsiveness parameter that is associated with an elevation of one or more limbs of the patient. For example, in some cases, some variance of a passive leg raise (PLR) test can be performed on the patient. As described herein, a PLR test is a non-invasive, bedside test, which can results in the elevation of one or more limbs (e.g., one or more legs) of the patient.

Figure 6A:
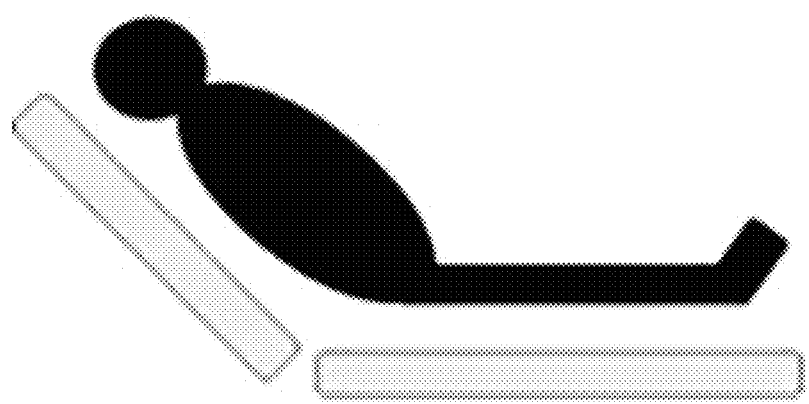
FIGS. 6A-6C illustrate embodiments of example GUIs that displays example graphics for instructing or implementing the PLR test on a patient.
Figure 6B:
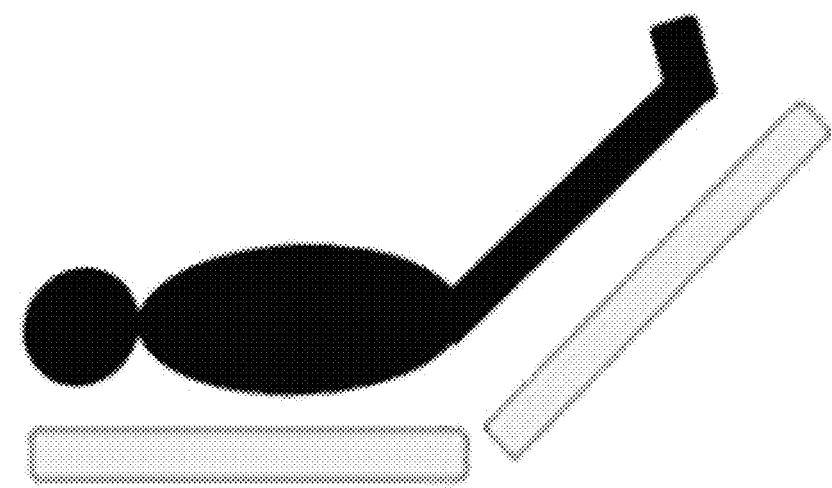
Figure 6C:
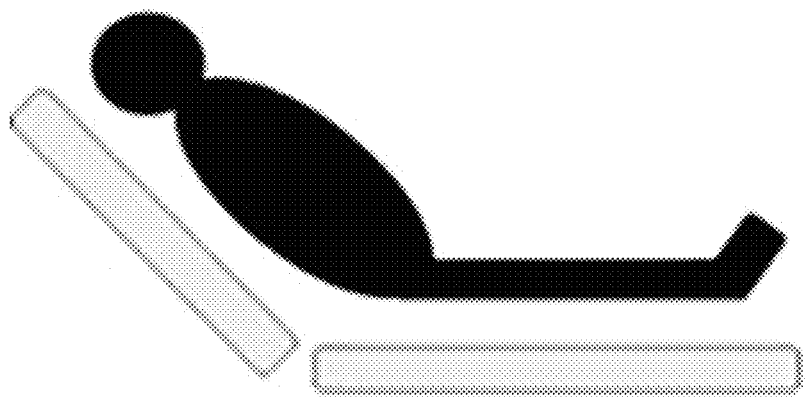
Figure 7:
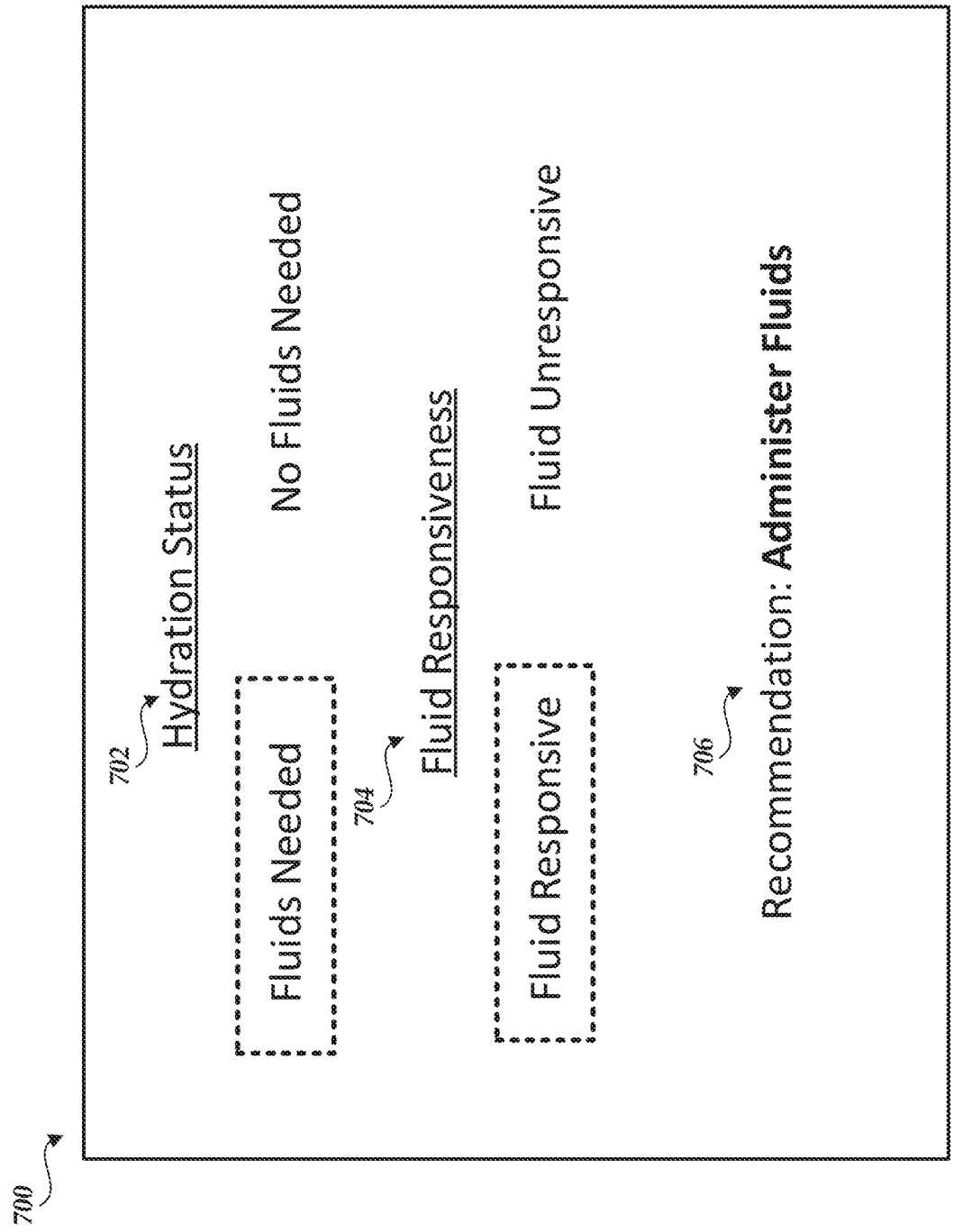
FIG. 7 illustrates an embodiment of an example GUI that displays a fluid administration recommendation based on the hydration status and/or fluid responsiveness of the patient.

In some cases, the PLR test can be automated or semi-automated. For example, the processor 104 can cause the PLR test to begin, for instance by controlling movement of a patient's bed. In some cases, the PLR test can be performed manually, such as by a physician. In some cases, the processor 104 can provide an instruction to perform the PLR test. The instruction can include an auditory, visual or other indication. In some cases, the processor 104 can provide instructions throughout the PLR test. For example, the processor 104 can generate a graphical user interface (GUI) that displays a graphical indication of one or more steps of the PLR test. In some cases, the processor 104 can cause a display (for example, display 106 or 224) to display a visual walkthrough of the steps of the PLR test. FIGS. 6A-6C illustrate an embodiment of an example GUI that displays example graphics for instructing or implementing the PLR test on a patient. As illustrated, for one or more steps of the PLR test, the GUI can show a graphical depiction of the orientation of the patient and/or the patient's bed. In addition or alternatively, the GUI can include instructions for the caregiver, such as an indication of when to obtain results from the PLR test, a timer or alarm for a particular step, or the like.

The fluid responsiveness parameter can vary across embodiments. For example, in some cases, the fluid responsiveness parameter includes a measure of cardiac output. As another example, in some cases, the fluid responsiveness parameter includes a measure of heart rate. As another example, in some cases, the fluid responsiveness parameter includes a measure of stroke volume. The fluid responsiveness parameter can be determined at one or more of various stages of the PLR test. For example, the fluid responsiveness parameter can be determined prior to performance of the PLR test, during the PLR test, and/or after the PLR test has completed. Furthermore, the fluid responsiveness parameter can be measured in real-time by one or more sensors and/or can be calculated by the processor 104 using sensor data. Alternatively, in some cases, a physician and/or medical device can monitor the fluid responsiveness parameter of the patient, and the physician can enter fluid responsiveness parameter as an input to the processor 104.

The processor 104 can determine a prediction of fluid responsiveness or unresponsiveness in various ways. For example, changes in the fluid responsiveness parameter can be used to guide the determination of the prediction. For example, in some cases, a first fluid responsiveness parameter is measured prior to during the PLR test and a second fluid responsiveness parameter is measured during or after PLR test. In some such cases, the processor 104 can determine a prediction of fluid responsiveness or unresponsiveness based one a comparison for the first fluid responsiveness parameter and the second fluid responsiveness parameter. For example, if the second fluid responsiveness parameter increases (for example, by a threshold amount) relative to the first fluid responsiveness parameter, then the processor 104 can determine a prediction of fluid responsiveness. Put another way, in some cases, if the PLR test causes the fluid responsiveness parameter to increase (for example, by a threshold amount), the processor 104 can determine a prediction of fluid responsiveness. As a corollary, in some cases, if the PLR test causes the fluid responsiveness parameter to stay the same, decrease, or not increase by threshold amount, the processor 104 can determine a prediction of fluid unresponsiveness.

In some cases, the processor 104 can further determine a confidence value associated with the prediction of fluid responsiveness or unresponsiveness. For example, in some cases, the confidence in a prediction of fluid responsiveness or unresponsiveness is based on the amount that the fluid responsiveness parameter changes over time. For example, for a prediction of fluid responsiveness, a relatively larger increase in the fluid responsiveness parameter can result in a higher confidence value, while a relatively smaller increase can result in a lower confidence value. As another example, for a prediction of fluid unresponsiveness, no increase or a decreases in the fluid responsiveness parameter can result in a higher confidence value, while an increase in the fluid responsiveness parameter can result in a lower confidence value.

At block 508, the processor 104 outputs an indication of an overall prediction of fluid responsiveness or fluid responsiveness. For example, the processor 104 can determine the overall prediction of fluid responsiveness or fluid responsiveness based at least in part on the determinations at block 506 and/or block 508. For example, the overall prediction of fluid responsiveness or fluid responsiveness can be based at least in part on one or more of the prediction of fluid responsiveness or unresponsiveness using the plethysmograph variability parameter, the prediction of fluid responsiveness or unresponsiveness using the fluid responsiveness parameter, and/or confidence values associated therewith.

As an example, if both blocks 506 and 508 return a prediction of fluid responsiveness, then the processor 104 can output an indication of fluid responsiveness. As an example, if both blocks 506 and 508 return a prediction of fluid unresponsiveness, then the processor 104 can output an indication of fluid unresponsiveness. In some cases, if one of blocks 506 and 508 returns a prediction of fluid unresponsiveness and one of blocks 506 and 508 returns a prediction of fluid unresponsiveness, then the processor 104 can output an error code. In some cases, if one of blocks 506 and 508 returns a prediction of fluid unresponsiveness and one of blocks 506 and 508 returns a prediction of fluid responsiveness, then the processor 104 can output the prediction of whichever method produced a higher confidence value, as described herein.

It will be understood that the various blocks described herein can be implemented in a variety of orders, and that the processor 104 can implement one or more of the blocks concurrently and/or change the order, as desired. For example, in some cases, any of blocks 502, 504, 506 and/or 508 can be implemented prior to or currently with any other blocks 502. Furthermore, it will be understood that fewer, more, or different blocks can be used as part of the routine 500. For example, the routine 500 can include blocks for controlling a device to administer fluids to the patient or terminate administration of fluids to the patient. For instance, in some cases, based on a prediction of fluid responsiveness, the processor can cause fluid to be administered to the patient, either by operating or controlling a medical device, such as an infusion pump, to administer fluids to the patient or by outputting an indication to administer fluids. As another example, in some cases, based on a prediction of fluid unresponsiveness, the processor can cause administration of fluid to be terminated, either by operating or controlling a medical device, such as an infusion pump, or by outputting an indication to termination administration of fluids.

Furthermore, the processor 104 can cause display on the GUI of one or more instructions, which, when viewed, can indicate how to perform the PLR test, or a duration over which to hold a specific step of the PLR test. Furthermore, in some cases, rather than or in addition to predicting fluid responsiveness or fluids unresponsiveness, the processor 104 can identify a hydration status of a patient. In some cases, if the patient is hydrated, the processor 104 doesn't initiate the routine 500. In some cases, the processor 104 initiates the routine 500 based on a determination that the patient is dehydrated. Furthermore, in some cases, the routine 500 can omit certain blocks, such as, but not limited to, blocks 502, 504, 506, and/or 508.

Terminology

The term "and/or" herein has its broadest least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The following description is merely illustrative in nature and is in no way intended to limit the disclosure, its application, or uses. For purposes of clarity, the same reference numbers will be used in the drawings to identify similar elements. It should be understood that steps within a method may be executed in different order without altering the principles of the present disclosure.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figures. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A patient monitoring device for determining fluid responsiveness of a patient, the patient monitoring device comprising:
   one or more of non-invasive physiological sensors configured to obtain physiological information from the patient, and further configured to emit light towards a tissue site of a patient, and detect the light after it has interacted with the tissue site, and generate a sensor signal based at least in part on the detected light;
   a sensor interface configured to receive the sensor signal from the one or more non-invasive physiological sensors; and
   a processor in communication with the sensor interface and configured to:
   automatically determine a plethysmograph variability parameter associated with a plethysmograph waveform corresponding to the sensor signal, wherein the plethysmograph waveform comprises a plurality of pulses corresponding to pulsatile blood flow within the tissue site, wherein the plethysmograph variability parameter corresponds to a value associated with a pleth variability index (PVI) and quantifies variations in the plethysmograph waveform,
   determine a first prediction of fluid responsiveness based at least in part on the plethysmograph variability parameter,
   determine a first confidence value associated with the first prediction of fluid responsiveness based on a value of the plethysmograph variability parameter,
   send a control signal to cause a bed of the patient to move in order to cause a change in elevation of one or more limbs of the patient,
   determine a second prediction of fluid responsiveness based at least in part on a fluid responsiveness parameter that is associated with an elevation of the one or more limbs of the patient that is associated with a passive leg raising (PLR) test,
   determine a second confidence value associated with the second prediction of fluid responsiveness based on a change in the fluid responsiveness parameter,
   output an indication of fluid responsiveness of the patient based at least in part on the first confidence value, the second confidence value, the first prediction of fluid responsiveness, and the second prediction of fluid responsiveness, and
   cause an action, based on the fluid responsiveness of the patient, related to administration of fluid to the patient.

2. The patient monitoring device of claim 1, wherein the fluid responsiveness parameter comprises a measure of at least one of cardiac output, heart rate, or stroke volume.

3. The patient monitoring device of claim 1, wherein the elevation of one or more limbs is performed prior to administration of fluids to the patient.

4. The patient monitoring device of claim 1, wherein the elevation of the one or more limbs is performed during administration of fluids to the patient.

5. The patient monitoring device of claim 1, wherein the treatment recommendation comprises at least one of a recommendation to administer the fluids to the patient, a recommendation to not administer the fluids to the patient, or a recommendation to terminate administration of the fluids to the patient.

* * * * *

UNITED STATES PATENT AND TRADEMARK OFFICE
CERTIFICATE OF CORRECTION

PATENT NO. : 12,004,869 B2
APPLICATION NO. : 16/673335
DATED : June 11, 2024
INVENTOR(S) : Massi Joe E. Kiani Page 1 of 1

It is certified that error appears in the above-identified patent and that said Letters Patent is hereby corrected as shown below:

On the Title Page

Column 1 (Item (54) Title), Line 3, delete "VARIABLITY" and insert -- VARIABILITY --.

Page 4, Column 1 (Item (56) U.S. Patent Documents), Line 25, delete "Ali et al." and insert -- Al-Ali et al. --.

Page 4, Column 2 (Item (56) U.S. Patent Documents), Line 23, delete "Bellot et al." and insert -- Bellott et al. --.

In the Specification

Column 1, Line 3 (Title), delete "VARIABLITY" and insert -- VARIABILITY --.

Column 6, Line 63, delete "CA" and insert -- CA. --.

Column 8, Line 2, delete "and or" and insert -- and/or --.

Column 13, Line 30, delete "can be can" and insert -- can be --.

Signed and Sealed this
Eighth Day of October, 2024

Katherine Kelly Vidal
*Director of the United States Patent and Trademark Office*